(12) United States Patent
Niwa et al.

(10) Patent No.: US 11,382,590 B2
(45) Date of Patent: Jul. 12, 2022

(54) RADIATION IMAGING APPARATUS, RADIATION IMAGING SYSTEM, CONTROL METHOD, AND STORAGE MEDIUM

(71) Applicant: CANON KABUSHIKI KAISHA, Tokyo (JP)

(72) Inventors: Hiroaki Niwa, Kawasaki (JP); Akiya Nakayama, Kawasaki (JP); Yuichi Nishii, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 387 days.

(21) Appl. No.: 16/717,372

(22) Filed: Dec. 17, 2019

(65) Prior Publication Data

US 2020/0205767 A1 Jul. 2, 2020

(30) Foreign Application Priority Data

Dec. 27, 2018 (JP) .............................. JP2018-245339
Sep. 27, 2019 (JP) .............................. JP2019-177549

(51) Int. Cl.
*A61B 6/00* (2006.01)
(52) U.S. Cl.
CPC .................................. *A61B 6/542* (2013.01)
(58) Field of Classification Search
CPC ........... A61B 6/542; A61B 6/487; A61B 6/44; A61B 6/54
USPC ......................................................... 378/62
See application file for complete search history.

(56) References Cited

U.S. PATENT DOCUMENTS

2014/0079310 A1* 3/2014 Nakatsugawa ........ A61B 6/487
382/132
2015/0163395 A1* 6/2015 Konishi ............... H04N 5/3535
348/230.1
2016/0161617 A1* 6/2016 Kawanabe ............... H04N 5/32
250/370.08
2018/0063933 A1* 3/2018 Okada ....................... G01T 1/17
2018/0129120 A1* 5/2018 Sato ....................... A61B 6/542
2018/0321397 A1* 11/2018 Kawanabe ............... A61B 6/42
2020/0205767 A1* 7/2020 Niwa ..................... A61B 6/542

FOREIGN PATENT DOCUMENTS

JP 2011-98009 A 5/2011
JP 2015-213546 A 12/2015

* cited by examiner

*Primary Examiner* — David P Porta
*Assistant Examiner* — Gisselle M Gutierrez
(74) *Attorney, Agent, or Firm* — Canon U.S.A., Inc. IP Division

(57) ABSTRACT

A radiation imaging apparatus includes an imaging area including a plurality of conversion elements configured to convert a radiation into an electrical signal, a detection element provided in the imaging area and configured to detect the radiation, a reading unit configured to read signals of the conversion elements and the detection element, and a control unit configured to execute radiation exposure amount control in capturing a radiation image by a control method selected from a first control method and a second control method based on an imaging condition in capturing the radiation image, the first control method controlling an exposure amount based on the reading result of the detection element read by the reading unit during radiation irradiation, the second control method controlling the exposure amount based on a pixel value of the radiation image, the radiation image being based on the signals of the plurality of conversion elements.

20 Claims, 10 Drawing Sheets

RADIATION IMAGING APPARATUS, RADIATION IMAGING SYSTEM, CONTROL METHOD, AND STORAGE MEDIUM

BACKGROUND

Field of the Disclosure

The present disclosure relates to a radiation imaging apparatus, a radiation imaging system, a control method, and a computer-storage medium storing a computer program.

Description of the Related Art

Detection apparatuses and radiation detection apparatuses using a matrix substrate have been put to practical use as imaging apparatuses for X-ray medical image diagnosis and nondestructive inspection. The matrix substrate includes a pixel array combining switch elements such as a thin-film transistor (TFT) and conversion elements such as a photoelectric conversion element. For example, in medical image diagnosis, such radiation imaging apparatuses are used as digital imaging apparatuses for capturing still images like general radiography and for capturing moving images like fluoroscopic imaging.

Making such detection apparatuses go multifunctional has been discussed in recent years. One of the approaches is to provide a detection apparatus with a built-in function for finding out irradiation information while a radiation source is emitting radiations. Finding out irradiation start timing at which the radiations are emitted from the radiation source, or finding out the amount of radiations and a cumulative exposure amount is an example of such a function. The detection apparatus can also monitor the cumulative exposure amount and, when the cumulative exposure amount reaches an appropriate amount, the apparatus controls the radiation source to end the irradiation. Such control is called automatic exposure control (AEC).

Japanese Patent Application Laid-Open No. 2015-213546 discusses a radiation imaging apparatus that obtains exposure dose information by reading charges accumulated in pixels during radiation irradiation, and issues an instruction to end the radiation irradiation based on the obtained exposure dose information and a target dose value.

Automatic brightness control (ABC) is another technique for obtaining an appropriate radiation image brightness. ABC is a technique for maintaining a constant brightness level by bringing an average pixel value or weighted average pixel value within a region of interest (ROI) of an X-ray image, closer to a target value. Specifically, in ABC, the conditions of radiations to be generated in the next and subsequent frames are changed based on the average value in the ROI. Japanese Patent Application Laid-Open No. 2011-98009 discusses a technique for improving the accuracy of the ABC.

However, the outputs of the pixels read during radiation irradiation include offset components due to dark charges occurring in the pixels and the reference potential of an amplifier integrated circuit (IC). In AEC, to obtain accurate exposure dose information, the offset components need to be obtained immediately before X-ray irradiation and subtracted from the outputs of each frame during irradiation. A preparatory driving sequence for obtaining the offset components is required in each frame. This reduces a necessary time for enabling charge accumulation, i.e., a necessary time for enabling X-ray irradiation in each frame, and it becomes difficult to carry out a desired imaging operation in high frame rate imaging.

ABC is a scheme including analysis of the obtained X-ray image and feedback of the analysis result to an X-ray generation apparatus, and thus makes high frame rate imaging possible. However, a delay occurs in terms of a control target frame since the analysis result is reflected on the next or subsequent frames. A first frame when the imaging is started, therefore, gets no feedback.

SUMMARY

Embodiments in the present disclosure are directed to appropriately controlling a radiation exposure amount.

According to an aspect of some embodiments, a radiation imaging apparatus includes an imaging area including a plurality of conversion elements configured to convert a radiation into an electrical signal, a detection element provided in the imaging area and configured to detect the radiation, a reading unit configured to read signals of the conversion elements and the detection element, and a control unit configured to execute radiation exposure amount control in capturing a radiation image by a control method selected from between a first control method and a second control method based on an imaging condition in capturing the radiation image, the first control method controlling an exposure amount of the radiation based on the signal of the detection element read by the reading unit during radiation irradiation, the second control method controlling the irradiation amount of the radiation based on a pixel value of the radiation image, the radiation image being based on the signals of the plurality of conversion elements read by the reading unit.

Further features of various embodiments will become apparent from the following description of exemplary embodiments with reference to the attached drawings.

DESCRIPTION OF THE EMBODIMENTS

Exemplary embodiments will be described below with reference to the drawings.

Figure 1:
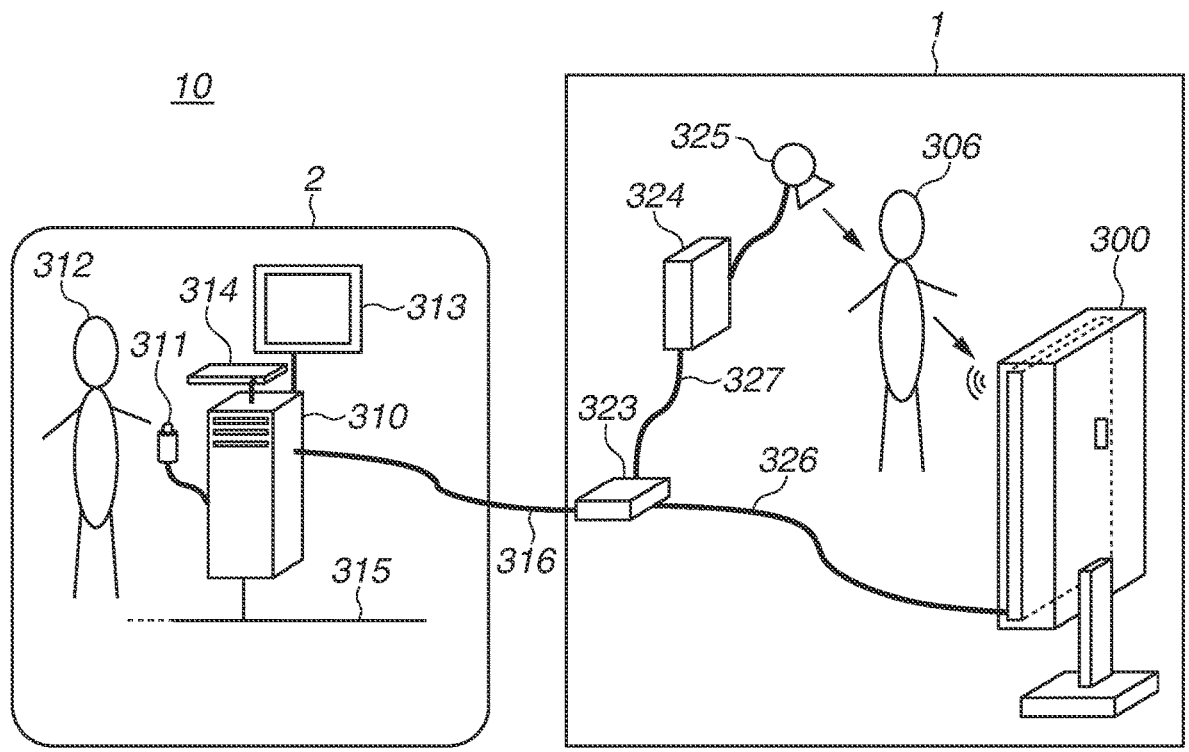
FIG. 1 is an overall diagram of a radiation imaging system.

FIG. 1 is an overall diagram of a radiation imaging system 10 according to a first exemplary embodiment. The radiation imaging system 10 includes a radiation imaging apparatus 300, a communication control apparatus 323, a radiation generation apparatus 324, a radiation source 325, an imaging apparatus cable 326, and a radiation generation apparatus communication cable 327. The radiation imaging apparatus 300, the communication control apparatus 323, the radiation generation apparatus 324, the radiation source 325, the imaging apparatus cable 326, and the radiation generation apparatus communication cable 327 are installed in a radiation room 1. If the radiation imaging apparatus 300 communicates wirelessly, an access point is provided instead of using the imaging apparatus cable 326.

The radiation imaging apparatus 300 also includes a control apparatus 310, a radiation irradiation switch 311, a display device 313, an input device 314, a hospital local area network (LAN) 315, and a radiation room communication cable 316. The control apparatus 310, the radiation irradiation switch 311, the display device 313, the input device 314, the hospital LAN 315, and the radiation room communication cable 316 are set up in a control room 2.

The radiation imaging apparatus 300 detects radiations transmitted through a subject 306 and generates radiation image data. The communication control apparatus 323 performs control to enable communication between the radiation generation apparatus 324 and the control apparatus 310. The radiation generation apparatus 324 controls the radiation source 325 to emit radiations based on an irradiation condition. The radiation source 325 irradiates the subject 306 with radiations under control of the radiation generation apparatus 324.

The imaging apparatus cable 326 is a cable for connecting the radiation imaging apparatus 300 with the communication control apparatus 323. The radiation generation apparatus communication cable 327 is a cable for connecting the radiation generation apparatus 324 with the communication control apparatus 323.

The control apparatus 310 communicates with the radiation generation apparatus 324 and the radiation imaging apparatus 300 via the communication control apparatus 323 and controls the radiation imaging system 10 in a centralized manner. The radiation irradiation switch 311 inputs the timing of radiation irradiation based on operation of an operator 312. The input device 314 is a device for inputting instructions from the operator 312. Various input devices, such as a keyboard and a touch panel, are used. The display device 313 is a device for displaying processed radiation image data and a graphical user interface (GUI). A display is used as the display device 313. The hospital LAN 315 is a backbone network in the hospital.

Next, an operation of the radiation imaging system 10 will be described. The control apparatus 310 initially sets subject information, such as an identifier (ID), name, and date of birth of the subject 306, and imaging information, such as an imaging site of the subject 306, based on operations of the operator 312. In another example, the operator 312 may select an inspection order received via the hospital LAN 315, and the control apparatus 310 may set imaging information specified by the selected inspection order. In another example, the control apparatus 310 may set imaging information by selecting a preset imaging protocol. The control apparatus 310 further identifies imaging conditions, such as an imaging frame rate and radiation irradiation time per frame, based on the set information.

Upon completion of the imaging preparations, the operator 312 presses the radiation irradiation switch 311. If the radiation irradiation switch 311 is pressed, after the radiation imaging apparatus 300 makes relevant preparations, the radiation source 325 emits radiations toward the subject 306. The radiation imaging apparatus 300 communicates with the radiation generation apparatus 324 to control the start and end of radiation irradiation. The radiations with which the subject 306 is irradiated are transmitted through the subject 306 and incident on the radiation imaging apparatus 300. The radiation imaging apparatus 300 converts the incident radiations into visible light and detects the visible light as a radiation image signal by using photoelectric conversion elements.

The radiation imaging apparatus 300 chives the photoelectric conversion elements to read the radiation image signal, and converts the analog signal into a digital signal via an analog-to-digital (AD) conversion circuit to obtain digital radiation image data. The obtained digital radiation image data is transferred from the radiation imaging apparatus 300 to the control apparatus 310. The control apparatus 310 performs image processing on the received digital radiation image data. The control apparatus 310 displays a radiation image based on the processed radiation image data on the display device 313. The control apparatus 310 functions as an image processing apparatus and a display control apparatus. The operation of the radiation imaging system 10 has been described.

Figure 2:
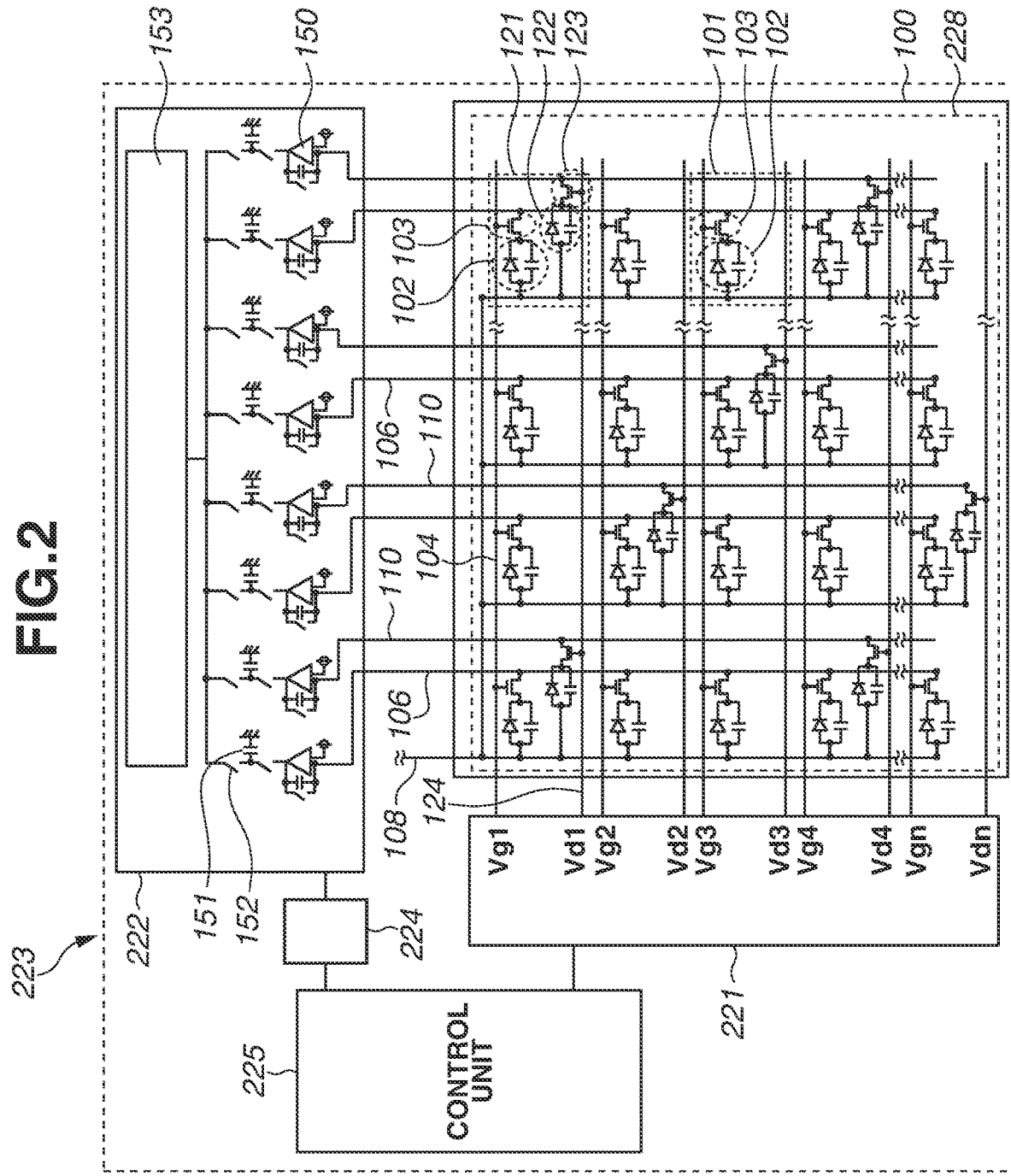
FIG. 2 is a configuration diagram of a detection unit.

FIG. 2 is a configuration diagram of a detection unit 223 included in the radiation imaging apparatus 300. The detection unit 223 includes a support substrate 100, a driving circuit 221, a reading circuit 222, and a control unit 225. A pixel array 228 is arranged on the support substrate 100. The pixel array 228 is an example of an imaging area. The pixel array 228 includes a plurality of pixels arranged in a matrix. The pixel array 228 includes first pixels 101 and second pixels 121. The first pixels 101 and the second pixels 121 will be described below.

To obtain a radiation image, the first pixels 101 each include a conversion element 102 that converts incident radiations or light into a charge corresponding to the incident amount and a switch element 103 that outputs the charge generated by the conversion element 102 to a signal line. For example, the conversion element 102 is an indirect conversion element including a scintillator that converts radiations into light and a photoelectric conversion element that converts the light converted by the scintillator into a charge. In another example, the conversion element 102 may be a direct conversion element that directly converts radiations into a charge. Examples of the switch element 103 include a thin-film transistor (TFT) using amorphous silicon or polycrystalline silicon. For example, the switch element 103 made of polycrystalline silicon may be used depending on desired TFT characteristics. The semiconductor material of the TFT is not limited to silicon, and other semiconductor materials, such as germanium and compound semiconductors, may be used.

A first main electrode of the switch element 103 is electrically connected to a first electrode of the conversion element 102. A bias line 108 is electrically connected to a second electrode of the conversion element 102. The second electrodes of a plurality of conversion elements 102 arranged along a column are commonly connected to a bias line 108. A common bias voltage is supplied to the bias lines 108 in the respective columns. The bias voltage is supplied to the bias lines 108 from a power supply circuit (not illustrated).

A signal line 106 is electrically connected to a second main electrode of the switch circuit 103. The second main electrodes of the switch elements 103 in pixels arranged along a column are commonly connected to a signal line 106. The signal line 106 is laid out for each pixel column. The signal lines 106 are electrically connected to the reading circuit 222. A drive line 104 is electrically connected to a control electrode of the switch element 103. A drive line 104 is commonly connected to the control electrodes of the switch elements 103 in first pixels 101 arranged along a row. Gate control voltages Vg1 to Vgn are applied from the driving circuit 221 to respective drive lines 104.

The second pixels 121 each include a detection element 122 and a switch element 123. The detection element 122 is an element that converts incident radiations or light into a charge corresponding to the incident amount to obtain the total amount of radiations incident during radiation irradiation. The switch element 123 is an element that outputs the charge generated by the detection element 122 to a signal line. Each second pixel 121 further includes a conversion element 102 and a switch element 103. The conversion element 102 and the switch element 103 of the second pixel 121 operate similarly to the conversion element 102 and the switch element 103 of the first pixel 101.

A first main electrode of the switch element 123 is electrically connected to a first electrode of the detection element 122. A bias line 108 laid in each column is electrically connected to a second electrode of the detection element 122. The second main electrodes of switch elements 123 arranged along a column are commonly connected to a detection line 110. The detection lines 110 are electrically connected to the reading circuit 222. A drive line 124 laid in each row is connected to a control electrode of the switch element 123. Gate control voltages Vd1 to Vdn are applied from the driving circuit 221 to the respective drive lines 124.

As illustrated in FIG. 2, the pixel array 228 according to the present exemplary embodiment includes a plurality of second pixels 121. Note that the pixel array 228 may include at least one second pixel 121, and the number and positions of second pixels 121 are not limited to the exemplary embodiment. If the second array 228 includes a plurality of second pixels 121, the amount of incident radiations may be detected by only one of the detection elements 122 in the plurality of second pixels 121 or by a plurality of the detection elements 122. In another example, the pixel array 228 does not need to include any second pixel 121. In such a case, the drive lines 104 may be driven during radiation irradiation to detect the total amount of incident radiations by the first pixels 101.

In the reading circuit 222, the signal lines 106 and the detection lines 110 are connected to the inverting input terminals of respective operational amplifiers 150. The inverting input terminal of each operational amplifier 150 is connected to the output terminal via a feedback capacitor, and the non-inverting input terminal is connected to a fixed potential. The operational amplifiers 150 function as charge-voltage conversion circuits. An AD converter 153 is connected to the subsequent stage of the operational amplifiers 150 via sample-and-hold circuits 151 and a multiplexer 152. The reading circuit 222 is a digital conversion circuit for converting the charges transferred from the conversion elements 102 of the first pixels 101 and the conversion elements 102 and detection elements 122 of the second pixels 121 via the signal lines 106 and the detection lines 110 into digital electrical signals. The reading circuit 222 may be configured by integrating the foregoing circuits. Alternatively, the reading circuits 222 may be configured circuit by circuit.

Figure 3:
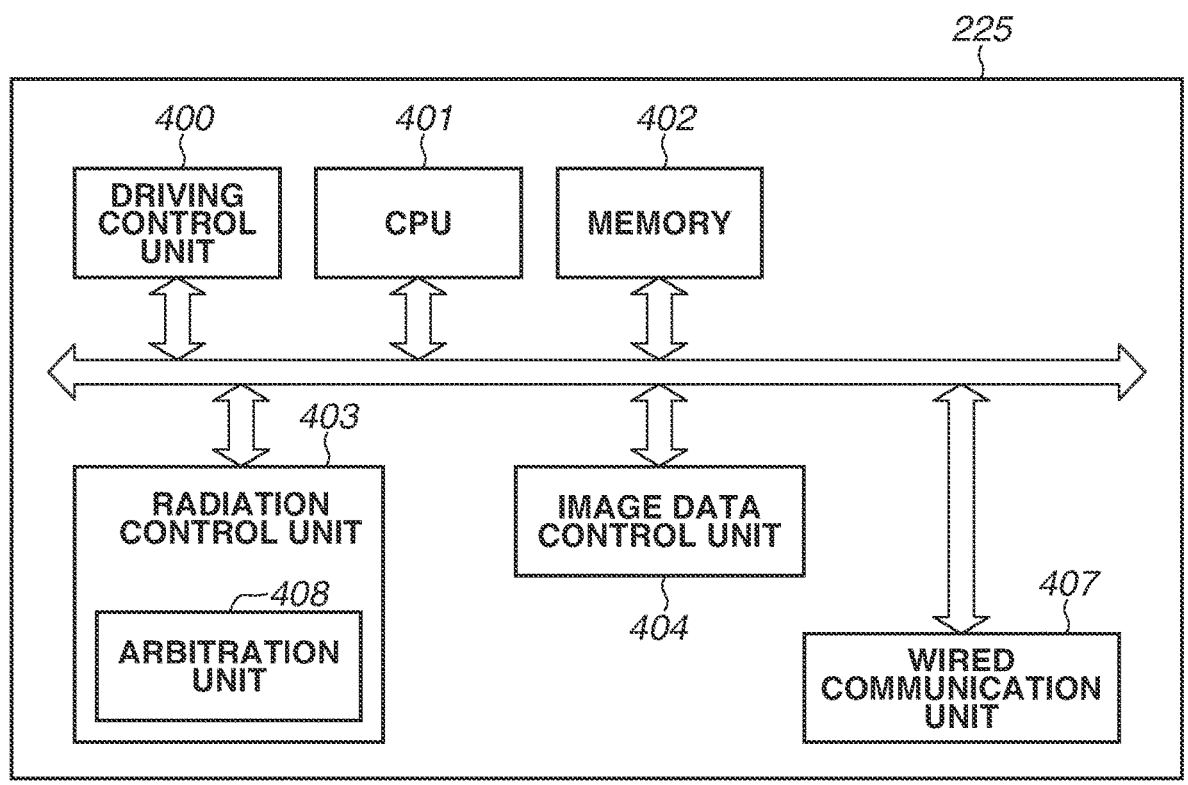
FIG. 3 is a block diagram of a control unit.

FIG. 3 is a block diagram of the control unit 225. The control unit 225 includes a driving control unit 400, a central processing unit (CPU) 401, a memory 402, a radiation control unit 403, an image data control unit 404, and a wired communication unit 407. The driving control unit 400 controls the driving circuit 221 and the reading circuit 222 based on information from the signal processing unit 224 and commands from the control apparatus 310. The commands include information about an imaging site. The CPU 401 controls the entire radiation imaging apparatus 300 by using programs and various types of data stored in the memory 402. For example, the memory 402 stores programs and various types of data that the CPU 401 uses in executing processing. The memory 402 also stores various types of data and radiation image data obtained in the processing by the CPU 401.

The radiation control unit 403 controls the radiation generation apparatus 324 based on information from the signal processing unit 224 and information from the driving control unit 400. The radiation control unit 403 exchanges control-related information (such as radiation irradiation start and end notifications, a radiation exposure amount, and a cumulative exposure amount) with the radiation generation apparatus 324 via the wired communication unit 407. The image data control unit 404 stores image data from the reading circuit 222 in the memory 402, and controls communication with the control apparatus 310. The image data control unit 404 and the control apparatus 310 exchange radiation image data and control-related information (for example, control commands). The wired communication unit 407 communicates with an external apparatus in a wired connection.

The functions and processing of the control unit 225 to be described below are implemented by the CPU 401 reading a program stored in the memory 402 and executing the program. In another example, the CPU 401 may read a program stored in a storage medium, such as a Secure Digital (SD) card, instead of the memory 402.

In another example, at least part of the functions and processing of the control unit 225 may be implemented by cooperation of a plurality of CPUs and memories. In another example, at least part of the functions and processing of the control unit 225 may be implemented by a hardware circuit.

Next, dose control operations (automatic exposure control (AEC) and automatic brightness control (ABC)) of the radiation imaging system 10 will be described. In performing radiation imaging, the operator 312 initially inputs irradiation conditions, a radiation detection region (region of interest (ROI)) that is the region to monitor radiations, and imaging site information into the control apparatus 310. Examples of the irradiation conditions include a dose, a maximum irradiation time, a tube current, and a tube voltage. The control apparatus 310 transmits the input irradiation conditions, radiation detection region (ROI), and imaging site information to the radiation imaging apparatus 300 and the radiation generation apparatus 324. Subsequently, if the imaging preparations are completed and the operator 312 presses the radiation irradiation switch 311, the radiation generation apparatus 324 emits radiations. The emitted radiations are transmitted through the subject 306 and incident on the radiation imaging apparatus 300.

Initially, AEC will be described. The radiation imaging apparatus 300 performs AEC using the incident radiations. The radiations incident on the ROI are detected by the detection elements 122, and the CPU 401 of the radiation imaging apparatus 300 calculates a cumulative exposure amount that is the cumulative value of doses (reached doses) detected in a predetermined period. The CPU 401 then determines radiation irradiation stop timing based on the cumulative exposure amount and an appropriate dose calculated from the imaging site and imaging conditions input by the operator 312.

The radiation control unit 403 notifies the radiation generation apparatus 324 to stop based on the determined radiation irradiation stop timing. The radiation generation apparatus 324 stops radiation irradiation based on the notified radiation irradiation stop timing. While the radiation imaging apparatus 300 issues the notification to stop radiation irradiation, such a configuration is not restrictive. The radiation imaging apparatus 300 may transmit a reached dose as a detection result at predetermined time intervals, and the radiation generation apparatus 324 may calculate the cumulative value of the reached doses.

Next, ABC will be described. The radiation imaging apparatus 300 calculates an average or weighted average pixel value (brightness) within a previously-set ROI in the image captured by radiation imaging. The calculation result is transmitted to the radiation generation apparatus 324. The radiation generation apparatus 324 reflects the calculation result on the irradiation conditions of the radiations related to the imaging of the next or sequent frames. AEC is an example of exposure control based on a reading result of pixels during radiation irradiation. ABC is an example of brightness control based on an analysis of obtained pixel values.

Figure 4:
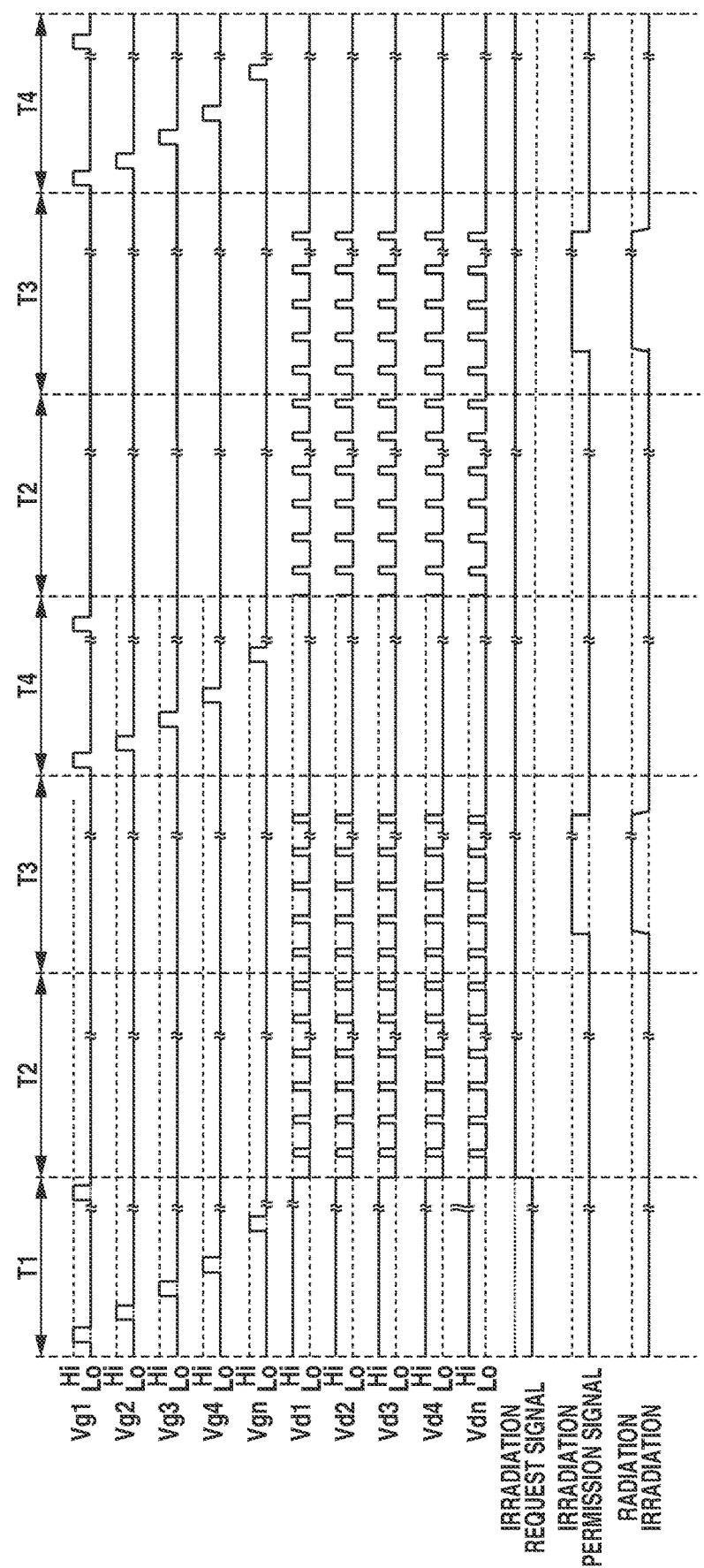
FIG. 4 is a timing chart during automatic exposure control (AEC).

FIG. 4 is a timing chart during AEC. A period T1 illustrated in FIG. 4 represents an idling period during standby. As illustrated in FIG. 4, in the period T1, the pixel array 228 repeats an idling operation based on the signals applied from the driving circuit 221. For example, the idling operation is performed after power-on of the detection unit 223 until acquisition of offset components is started. The period T1 includes the time during which the user inputs imaging information and the time before the user presses the radiation irradiation switch 311.

In the period T1, to remove dark currents occurring from the conversion elements 102 on a regular basis, a high (Hi) signal is periodically applied to the gate control voltages Vg1 to Vgn to scan the switch elements 103 of the first pixels 101. Similarly, to remove dark currents occurring from the detection elements 122 of the second pixels 121, a Hi signal is constantly applied to the gate control voltages Vd1 to Vdn to maintain the switch elements 123 of the second pixels 121 in a conducting state. As employed herein, a Hi signal has a voltage that turns on the switch elements 103 and 123. A low (Lo) signal has a voltage that turns off the switch elements 103 and 123 (for example, 0 V).

The timing chart of FIG. 4 corresponds to a case where a plurality of detection elements 122 are used to detect the amount of incident radiations. In such a case, the plurality of detection elements 122 is set to the same target radiation amount. The target radiation amount is calculated by the control unit 225 based on the imaging site and the imaging conditions. If the detection value of at least one of the detection elements 122 reaches the target radiation amount, the control unit 225 outputs a stop signal.

In another example, the control unit 225 may output the stop signal if the detection values of all the detection elements 122 reach the target radiation amount, or if an average of the detection values of all the detection elements 122 reaches the target radiation amount. In another example, the plurality of detection elements 122 may be set to respective different target radiation amounts. The target radiation amount(s) of the detection elements 122 and the condition for the control unit 225 to output the stop signal are set as appropriate depending on the imaging object, the imaging conditions, and the positions of the detection elements 122 in the pixel array 228.

Next, if the radiation irradiation switch 311 is pressed, the radiation imaging apparatus 300 receives an irradiation request signal. If the radiation imaging apparatus 300 receives the irradiation request signal, the period T1 transitions to a period T2. The period T2 is a period for obtaining offset components. In the period T2, the gate control voltages Vd1 to Vdn are turned on at constant cycles to obtain offset components in a state of no radiation irradiation. As employed herein, the offset components include crosstalk and dark currents. The number of times to turn on the gate control voltages Vd1 to Vdn is determined in advance. The cycles of turning on the gate control voltages Vd1 to Vdn are the same as the cycles of detecting radiation signals during radiation irradiation. If the same driving is carried out, the values of offset signal amounts at the time of acquiring the offset components can be brought closer to those of the offset signal amounts in the detection signals during radiation irradiation. This enables more accurate correction of the offset components.

After the acquisition of the offset components ends, the period T2 transitions to a period T3. The period T3 is a period where radiations are emitted to obtain a radiation image. In the present exemplary embodiment, the radiation generation apparatus 324 starts actual radiation irradiation by receiving an irradiation permission signal from the radiation imaging apparatus 300. In the period T3, the Lo signal is applied to the gate control voltages Vg1 to Vgn that drive the switch elements 103, and the conversion elements 102 accumulate charges corresponding to the amounts of incident radiations. Meanwhile, the Hi signal is applied to the gate control voltages Vd1 to Vdn that drive the switch elements 123 at constant detection cycles, whereby the charges detected by the detection elements 122 are transmitted to the reading circuit 222 via the detection lines 110. The reading circuit 222 supplies the electrical signals based on the detected charges to the control unit 225 via the signal processing unit 224. The control unit 225 obtains the amounts of radiations incident on the detection elements 122 in each detection cycle. In the periods T2 to T3, the switch elements 123 continue to be driven in the same cycles. If the detection cycle changes or the detection stops temporarily upon the transition from the period T2 to the period T3, unintended signal variations occur due to the switching of the driving. This can affect the detection signals in the initial stage of the period T3 and cause a drop in the detection accuracy.

In FIG. 4, the gate control voltages WI to Vdn applied to the control electrodes of the switch elements 123 are the Hi signal at the same time. However, the operation in the period T2 is not limited thereto. For example, the gate control voltages Vd1 to Vdn corresponding to the switch elements 123 of the detection elements 122 connected to the same respective detection lines 110 may be divided into the Hi signals at different timings. This can increase the spatial resolution of the detection region although the amount of signals readable at a time is decreased. The offset components of the detection elements 122 are obtained in the same cycles as the driving cycles of the respective switch elements 123.

The charges transmitted from the detection elements 122 to the reading circuit 222 are converted into voltage information by the operational amplifiers 150. The voltage information is then sampled by the sample-and-hold circuits 151 based on the detection cycles, and converted into an electrical signal of digital data by the AD converter 153 via the multiplexer 152.

By using the obtained offset components, the control unit 225 corrects the radiation amounts that are detected by the detection elements 122 and converted from charges into electrical signals. The control unit 225 then makes a radiation exposure stop determination based on the cumulative values of the corrected radiation amounts (cumulative exposure amounts) and the target radiation amounts. If the cumulative values of the irradiated radiations reach the target radiation amounts or are expected to reach the target radiation amounts, the control unit 225 outputs a radiation irradiation stop signal to the radiation generation apparatus 324. The radiation generation apparatus 324 stops the radiation irradiation from the radiation source 325.

The duration of the period T3 is set based on an imaging mode and an irradiation time input in advance. For example, the control unit 225 performs control to stop radiation irradiation even if the target radiation amounts are not reached as described above when the irradiation time reaches its upper limit input as irradiation information. After the cumulative values of the radiation amounts detected by the detection elements 122 reach the target radiation amounts or after a predetermined time has elapsed, the period T3 transitions to a period T4.

The period T4 is a period for obtaining a captured radiation image after the radiation irradiation. During the period T4, the control unit 225 outputs control signals for reading out the signal charges stored in the conversion elements 102, to the driving circuit 221. The driving circuit 221 sequentially applies the Hi signal to the gate control voltages Vg1 to Vgn based on the control signals, whereby the switch elements 103 of the first pixels 101 and second pixels 121 are scanned in succession. The charges accumulated in the conversion elements 102 are converted into voltage information by the operational amplifiers 150, sampled by the sample-and-hold circuits 151, and converted into an electrical signal of digital data by the AD converter 153 via the multiplexer 152. The control unit 225 forms a radiation image based on the electrical signal obtained by and read from the conversion elements 102. The operation from the period T2 to the period T4 is repeated for a desired number of imaging frames, and the imaging ends.

Figure 5:
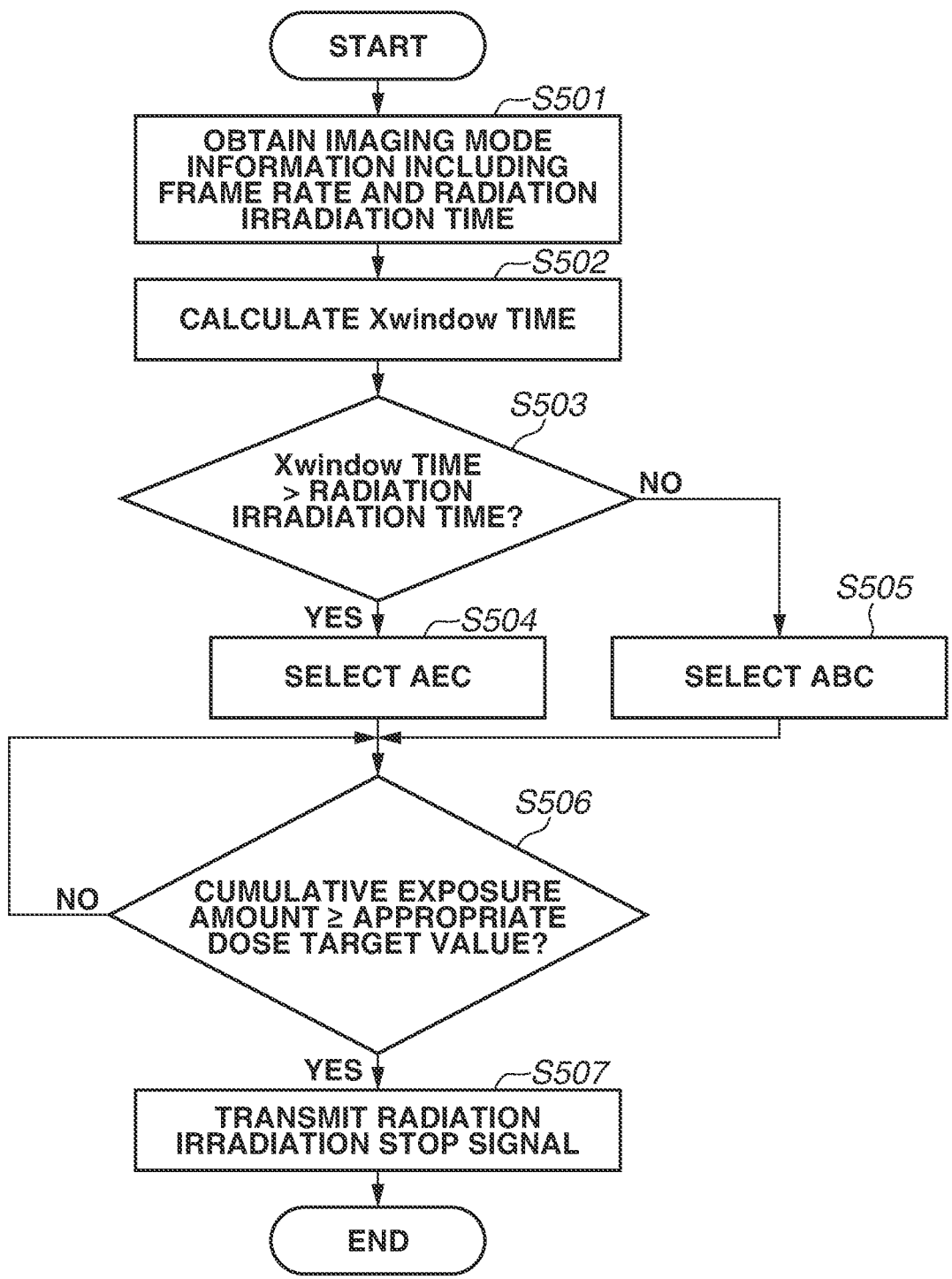
FIG. 5 is a flowchart illustrating radiation amount control processing.

FIG. 5 is a flowchart illustrating radiation amount control processing by the control unit 225. In S501, the CPU 401 of the control unit 225 obtains imaging mode information from the control apparatus 310. The imaging mode information is information indicating the imaging mode, and includes a frame rate and a radiation irradiation time. The imaging mode will now be described. Appropriate imaging conditions vary from one imaging site to another, like the front part of the head to a side part of the head to the cervical spine. The imaging conditions include a tube current, a tube voltage, an imaging time, and an irradiation field size. The imaging conditions vary with the body thickness in the measurement direction. The imaging conditions also vary between adults and children. Such subject conditions contributing to the imaging conditions are previously set in the control apparatus 310 as an imaging mode. The imaging conditions are set in association with the imaging mode.

For example, in the present exemplary embodiment, the display device 313 displays a list of imaging modes before a start of imaging. The user selects an imaging mode corresponding to the imaging to be performed, from the list. The control apparatus 310 accepts an imaging mode selection instruction corresponding to the user operation. The control apparatus 310 then generates image mode information corresponding to the imaging mode designated by the selection instruction. The imaging mode information includes the frame rate, radiation irradiation time, and imaging conditions corresponding to the imaging mode.

In the present exemplary embodiment, the control unit 225 receives the imaging mode information from the control apparatus 310. However, the processing for the control unit 225 to obtain the imaging mode information is not limited to such an exemplary embodiment. In another example, the control unit 225 may receive information indicating the imaging mode designated by the selection instruction from the control apparatus 310. In such a case, the control unit 225 may store a table associating imaging modes with imaging conditions and generate the imaging mode information based on the received information by referring to the table.

In S502, the CPU 401 calculates a time which enables accumulation (Xwindow time) for AEC based on the frame rate obtained in S501. The Xwindow time is a time calculated by subtracting an AEC offset data acquisition time and an image reading time from an imaging cycle time based on the frame rate.

In S503, the CPU 401 compares the Xwindow time with the radiation irradiation time obtained in S501. If the Xwindow time is greater than the radiation irradiation time (YES in S503), the processing proceeds to S504. If the Xwindow time is less than or equal to the radiation irradiation time (NO in S503), the processing proceeds to S505. In S504, the CPU 401 selects AEC as a method for controlling the radiation amount. In such a case, the CPU 401 performs AEC. In S505, the CPU 401 selects ABC as the method for controlling the radiation amount. In such a case, the CPU 401 performs ABC. AEC and ABC are as described above. The irradiation conditions at the beginning of control in performing AEC and in performing ABC are determined in advance.

If the Xwindow time is greater than the radiation irradiation time, radiation irradiation can be completed within the Xwindow time. The radiation imaging apparatus 300 therefore performs AEC in such a case. By contrast, if the Xwindow time is less than or equal to the radiation irradiation time, radiation irradiation cannot be completed within the Xwindow time. In other words, AEC cannot be performed in such a case. The radiation imaging apparatus 300 therefore performs ABC in such a case. This enables radiation amount control afterward, whereas feedback control is not available in the first few frames. Performing ABC can also avoid a situation where radiation irradiation cannot be completed within the Xwindow time like when AEC is performed. The relationship between the Xwindow time and the radiation irradiation time depends on the imaging conditions. In other words, the processing of S503 to S505 is an example of control processing for performing radiation amount control based on the imaging conditions.

In S506, the CPU 401 continues AEC or ABC until a cumulative exposure amount becomes greater than or equal to an appropriate dose (target radiation amount). If the cumulative exposure amount is greater than or equal to an appropriate dose target value (target radiation amount) (YES in S506), the processing proceeds to S507. In ABC, the CPU 401 here compares the cumulative exposure amount with the target radiation amount by using a reference target radiation amount set in the memory 402 in advance as the target radiation amount. In S507, the CPU 401 transmits the radiation irradiation stop signal to the radiation generation apparatus 324 via the wired communication unit 407. The radiation generation apparatus 324 in response controls the radiation source 325 to stop radiation irradiation. The radiation amount control processing ends.

As described above, in the present exemplary embodiment, the radiation imaging apparatus 300 determines the method for radiation control based on the Xwindow time and the radiation irradiation time. The radiation imaging apparatus 300 can thereby appropriately control the radiation exposure amount based on the imaging conditions.

Next, a radiation imaging system 10 according to a second exemplary embodiment will be described. The following description will deal mainly with differences from the radiation imaging system 10 according to the first exemplary embodiment. In the radiation imaging system 10 according to the second exemplary embodiment, a radiation imaging apparatus 300 performs both ABC and AEC in S505 (FIG. 5) for a predetermined period immediately after start.

Figure 6:
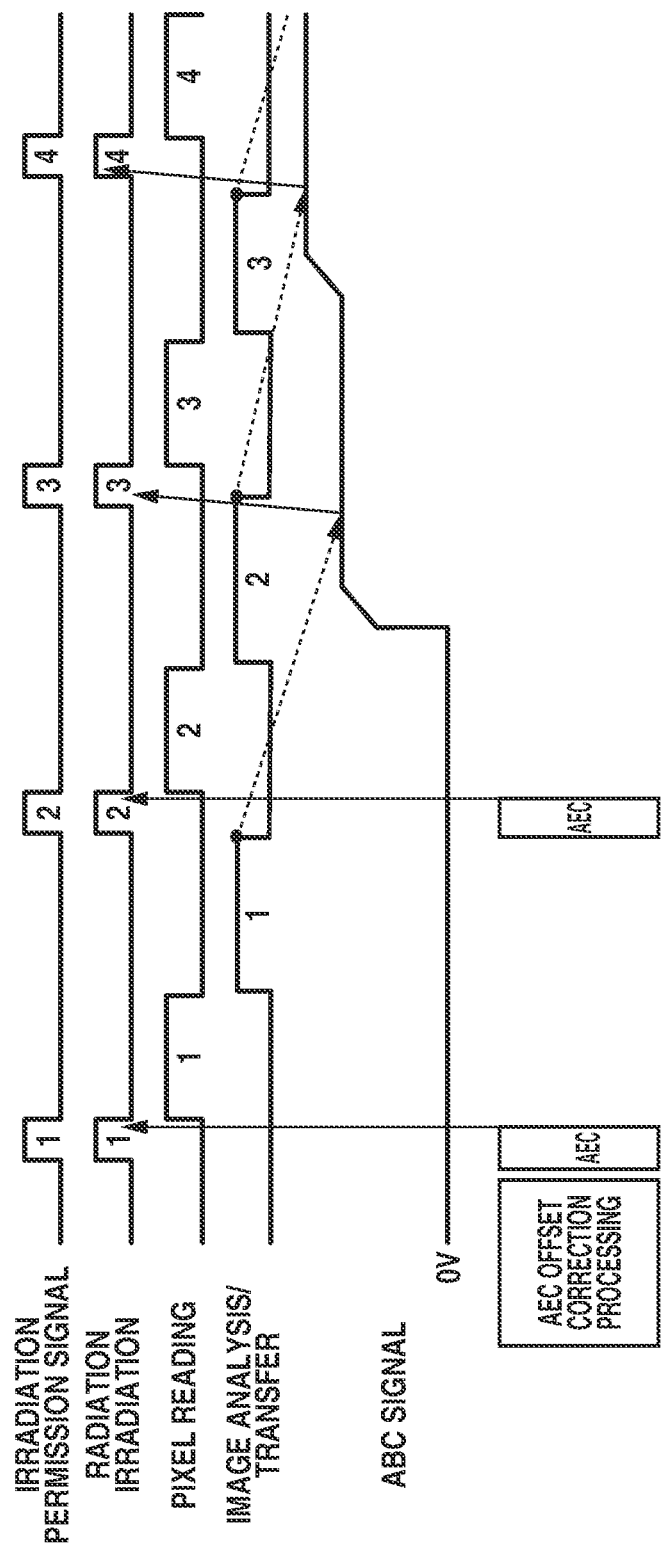
FIG. 6 is a timing chart of processing of S505 in FIG. 5.

FIG. 6 is a timing chart of the processing of S505 according to the second exemplary embodiment. In the second exemplary embodiment, a control unit 225 starts both ABC and AEC at radiation irradiation start timing Tx.

ABC is not available in the frames immediately after start. In the example of FIG. 6, the analysis result of the radiation image obtained by the first imaging operation is reflected on the third imaging operation, and dose control cannot be performed in the first and second imaging operations. By contrast, AEC can perform dose control even in the frames immediately after start. In the present exemplary embodiment, the control unit 225 therefore performs AEC along with ABC. In the example of FIG. 6, AEC is applied to the first and second imaging operations, and ABC is applied to the third and subsequent imaging operations. This enables radiation amount control on the frames immediately after start even in the processing of S505.

When the processing of S505 is performed, as it has been determined that the Xwindow time is less than or equal to the radiation irradiation time in the immediately preceding S503, the Xwindow time is insufficient. In the present exemplary embodiment, the control unit 225, in performing the processing of S505, therefore performs AEC offset correction processing in advance before the radiation irradiation start timing Tx as illustrated in FIG. 6. The AEC offset correction processing refers to processing for determining offset components and setting the offset components in a memory 402. During the AEC performed at and after the radiation irradiation starting timing Tx, the control unit 225 uses the already-obtained offset components. In other words, the control unit 225 performs no offset correction processing at or after the radiation irradiation start timing Tx. While the AEC offset components obtained in advance are susceptible to a state change such as a temperature change of the detection unit 223, correction can be made with desired accuracy if made in a short period. In such a manner, the Xwindow time can be increased by performing the AEC offset correction processing before the start of the radiation irradiation. The configuration and processing of the radiation imaging system 10 according to the second exemplary embodiment are similar to those of the radiation imaging system 10 according to the first exemplary embodiment.

As described above, in the second exemplary embodiment, the radiation imaging apparatus 300, when performing ABC, also performs AEC for a predetermined period after the start of imaging. This enables dose control from immediately after the start of radiation imaging. Further, the AEC is stopped and the dose control is switched to ABC at and after the timing that the irradiation conditions are set based on ABC. This can avoid the situation where radiation irradiation cannot be completed even if the Xwindow time is less than or equal to the radiation irradiation time. In such a manner, dose control suitable for each frame can be performed from the first frame to the end of imaging.

The period to perform AEC can be a predetermined period after the start of imaging and is not limited to the exemplary embodiment.

While respective analysis ROIs can be set for AEC and ABC, the same ROI is desirably set for both controls. In other words, the target region of AEC and that of ABC are desirably the same. Feedback information obtained by AEC and feedback information obtained by ABC for the same cumulative dose value may indicate different numerical values depending on the differences between the correction methods and the signal processing circuits. As employed herein, feedback information refers to a control value related to dose control. In such a case, the control unit 225 may use respective different thresholds for the appropriate dose target value.

In another example, the control unit 225 may obtain and store correlation data between the two controls in advance, and determine the appropriate dose target value (threshold) of either one of AEC and ABC, from the target value of the other. In the foregoing exemplary embodiment, there is an advantage that correlation between the two controls becomes more accurate since the imaging system for obtaining information by AEC and the imaging system of obtaining information by ABC are the same.

A third exemplary embodiment will be described below. A radiation exposure amount control (AEC) operation of a radiation imaging system 10 using a radiation imaging apparatus 300 will initially be described. An operator 312 inputs a maximum irradiation time, a radiation ROI that is the region for monitoring radiations, site information, and physical status information into a control apparatus 310. The control apparatus 310 transmits the input information to a radiation control unit 403 and a radiation generation apparatus 324. When imaging preparations are completed and a radiation irradiation switch 311 is pressed by the operator 312, radiations are emitted. The emitted radiations are transmitted through a subject 306 and incident on the radiation imaging apparatus 300. The radiation control unit 403 detects the radiations incident on the radiation ROI by using detection elements 122. A signal processing unit 224 calculates a cumulative exposure amount that is the cumulative value of doses (reached doses) detected in a predetermined period. The control unit 225 calculates an appropriate dose from cumulative exposure amount information from the signal processing unit 224, and determines radiation irradiation stop timing. The radiation control unit 403 notifies the radiation generation apparatus 324 of radiation stop timing based on the determined radiation irradiation stop timing. The radiation generation apparatus 324 stops radiation irradiation based on the notified radiation stop timing.

Next, a radiation brightness control (ABC) operation of the radiation imaging system 10 using the radiation imaging apparatus 300 will be described. The operator 312 inputs a target brightness value, a calculation formula expressing how to increase or decrease a tube current or tube voltage to bring pixel values closer to the target brightness value, and a radiation ROI that is the region for monitoring radiations, into the control apparatus 310. The control apparatus 310 transmits the input information to the radiation control unit 403. When imaging preparations are completed and the radiation irradiation switch 311 is pressed by the operator 312, radiations are emitted. The emitted radiations are transmitted through the subject 306 and incident on the radiation imaging apparatus 300. The radiation control unit 403 detects the radiations incident on the radiation ROI by using the pixels 101 and calculates an average pixel value within the ROI of the obtained image. The radiation control unit 403 transmits a feedback value of the calculation result of the calculation formula such that the average pixel value approaches the target brightness value, to the radiation generation apparatus 324. Based on the feedback value, the radiation generation apparatus 324 corrects the tube current or tube voltage to adjust the radiation brightness to an appropriate value in the next and subsequent frames.

As described above, AEC is a technique for stopping radiations when an appropriate amount is reached. ABC is a technique for adjusting a radiation condition (tube current or tube voltage) to obtain a radiation image of appropriate brightness. The radiation imaging apparatus 300 can have built-in functions for both AEC and ABC, and simultaneously use both the functions. This can simplify the configuration of the radiation imaging apparatus 300, and enables AEC and ABC operations in wireless and various other use positions including tabletop use.

However, if both AEC and ABC functions are built in the radiation imaging apparatus 300, the two functions can operate in a conflicting manner. For example, the radiation imaging apparatus 300 can attempt to stop radiations in response to an AEC-based determination that the appropriate amount is reached, while an ABC-based determination is to increase the radiation condition. With such conflicting operations, the radiation imaging apparatus 300 can fail to obtain an appropriate radiation image.

In the third exemplary embodiment, the radiation imaging apparatus 300 includes an arbitration unit capable of arbitrating between the AEC and ABC functions, and thereby prevents the two functions from making conflicting operations.

Figure 7:
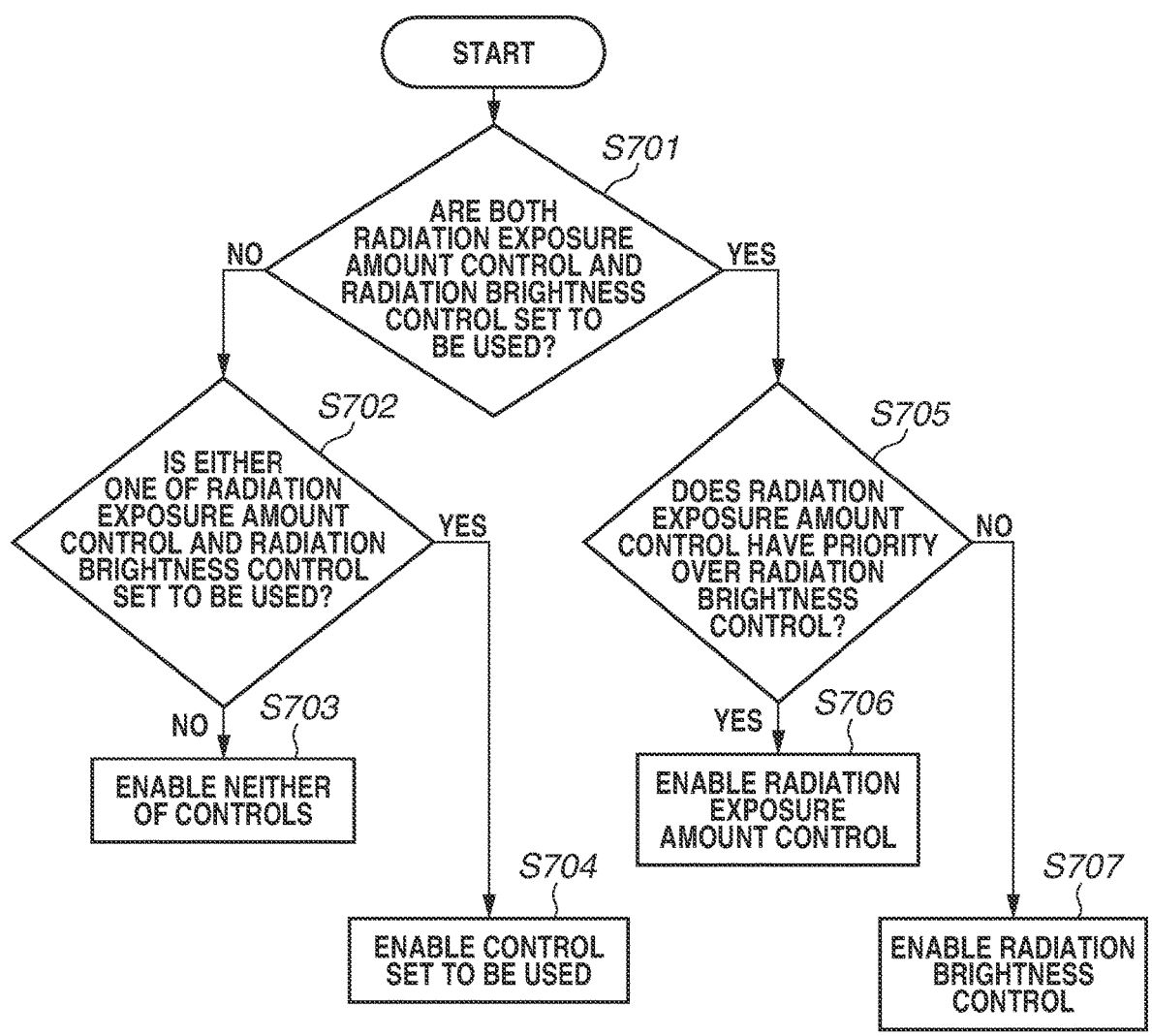
FIG. 7 is a flowchart illustrating a control method of an arbitration unit.

FIG. 7 is a flowchart illustrating a control method of the radiation control unit 403 according to the third exemplary embodiment. As illustrated in FIG. 3, the radiation control unit 403 includes an arbitration unit 408 that arbitrates between radiation exposure amount control and radiation brightness control.

In S701, the arbitration unit 408 determines whether use of both the radiation exposure amount control and the radiation brightness control are set, based on information from the control apparatus 310. If the use of both the radiation exposure amount control and the radiation brightness control are not set (NO in S701), the processing proceeds to S702. If the use of both the radiation exposure amount control and the radiation brightness control are set (YES in S701), the processing proceeds to S705.

In S702, the arbitration unit 408 determines whether either one of the radiation exposure amount control and the radiation brightness control is set to be used, based on the information from the control apparatus 310. If neither of the radiation exposure amount control and the radiation brightness control is used (NO in S702), the processing proceeds to S703. If either one of the radiation exposure amount control and the radiation brightness control is set to be used (YES in S702), the processing proceeds to S704.

In S703, the arbitration unit 408 enables neither of the radiation exposure amount control and the radiation brightness control.

In S704, the arbitration unit 408 enables the control operation which is set to be used, with respect to the radiation exposure amount control and the radiation brightness control.

In S705, the arbitration unit 408 determines whether the radiation exposure amount control has priority over the radiation brightness control, based on information from the control apparatus 310. If the radiation exposure amount control has priority over the radiation brightness control (YES in S705), the processing proceeds to S706. If the radiation brightness control has priority over the radiation exposure amount control (NO in S705), the processing proceeds to S707.

In S706, the arbitration unit 408 enables the radiation exposure amount control without enabling the radiation brightness control.

In S707, the arbitration unit 408 enables the radiation brightness control without enabling the radiation exposure amount control.

The radiation imaging apparatus 300 can prevent execution of the conflicting operations due to simultaneous operations of both the radiation exposure amount control and the radiation brightness control, such as attempting to reduce the amount of radiations by stopping irradiation based on the radiation exposure amount control and attempting to increase the amount of radiations based on the radiation brightness control. The radiation imaging apparatus 300 can thus obtain an appropriate radiation image.

Figure 8:
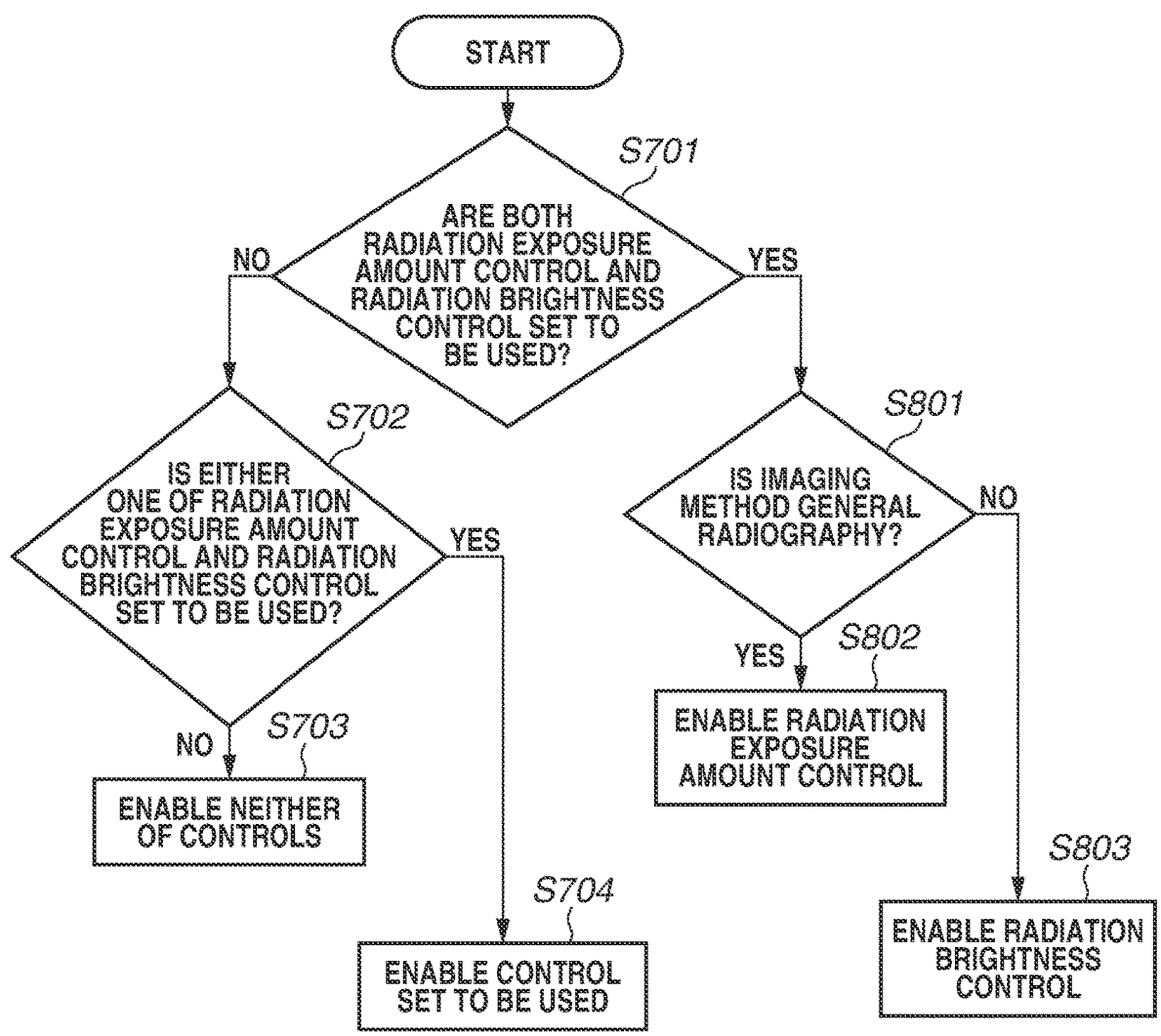
FIG. 8 is a flowchart illustrating a control method of the arbitration unit.

A fourth exemplary embodiment will be described below. FIG. 8 is a flowchart illustrating a control method of an arbitration unit 408 according to the fourth exemplary embodiment. FIG. 8 provides S801 to S803 instead of S705 to S707 of FIG. 7. Differences of the fourth exemplary embodiment from the third exemplary embodiment will be described below.

S701 to S704 are similar to those of FIG. 7. In S701, if the use of both the radiation exposure amount control and the radiation brightness control are set (YES in S701), the processing proceeds to S801.

In S801, the arbitration unit 408 determines whether the imaging method is general radiography (including still image capturing and continuous imaging), based on information from the control apparatus 310. If the imaging method is general radiography (YES in S801), the processing proceeds to S802. If the imaging method is fluoroscopic imaging (moving image capturing) (NO in S801), the processing proceeds to S803.

In S802, the arbitration unit 408 enables the radiation exposure amount control without enabling the radiation brightness control. In general radiography, the radiation exposure amount control is enabled since radiation irradiation is performed under constant radiation conditions determined in advance by fluoroscopic imaging.

In S803, the arbitration unit 408 enables the radiation brightness control without enabling the radiation exposure amount control. In fluoroscopic imaging, the radiation brightness control is enabled since the radiation brightness control has a role of appropriately adjusting the radiation conditions by weak radiation irradiation before imaging.

Figure 9:
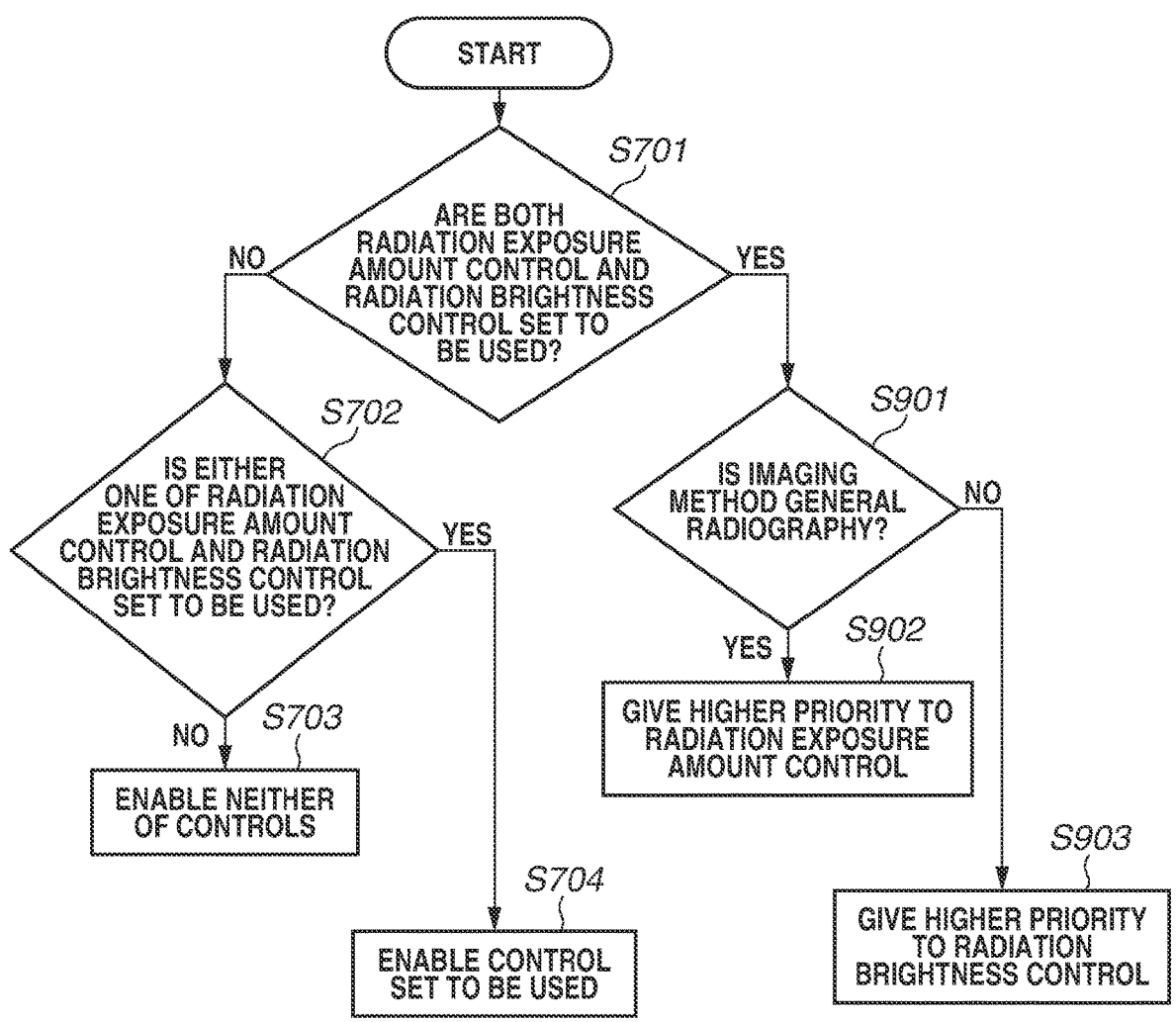
FIG. 9 is a flowchart illustrating a control method of the arbitration unit.

A fifth exemplary embodiment will be described below. FIG. 9 is a flowchart illustrating a control method of an arbitration unit 408 according to the fifth exemplary embodiment. FIG. 9 provides S901 to S903 instead of S705 to S707 of FIG. 7. Differences of the fifth exemplary embodiment from the third exemplary embodiment will be described below.

S701 to S704 are similar to those of FIG. 7. In S701, if the use of both the radiation exposure amount control and the radiation brightness control are set (YES in S701), the processing proceeds to S901.

In S901, the arbitration unit 408 determines whether the imaging method is general radiography (including still image capturing and continuous imaging), based on information from the control apparatus 310. If the imaging method is general radiography (YES in S901), the processing proceeds to S902. If the imaging method is fluoroscopic imaging (moving image capturing) (NO in S901), the processing proceeds to S903.

In S902, the arbitration unit 408 uses both the radiation exposure amount control and the radiation brightness control, with higher priority given to the radiation exposure amount control than to the radiation brightness control. Various methods may be used to give higher priority to the radiation exposure amount control. For example, the arbitration unit 408 calculates a brightness control formula to prevent the radiation irradiation time from falling below a minimum irradiation time, so that appropriate radiation irradiation is performed even during continuous imaging. The arbitration unit 408 then arbitrates to use both the radiation exposure amount control and the radiation brightness control.

In S903, the arbitration unit 408 uses both the radiation exposure amount control and the radiation brightness control, with higher priority given to the radiation brightness control than to the radiation exposure amount control. Various methods may be used to give higher priority to the radiation brightness control. For example, the arbitration unit 408 calculates an exposure amount so that the tube current or voltage does not fall below a minimum tube current or voltage. The arbitration unit 408 then arbitrates to use both the radiation exposure amount control and the radiation brightness control.

Figure 10:
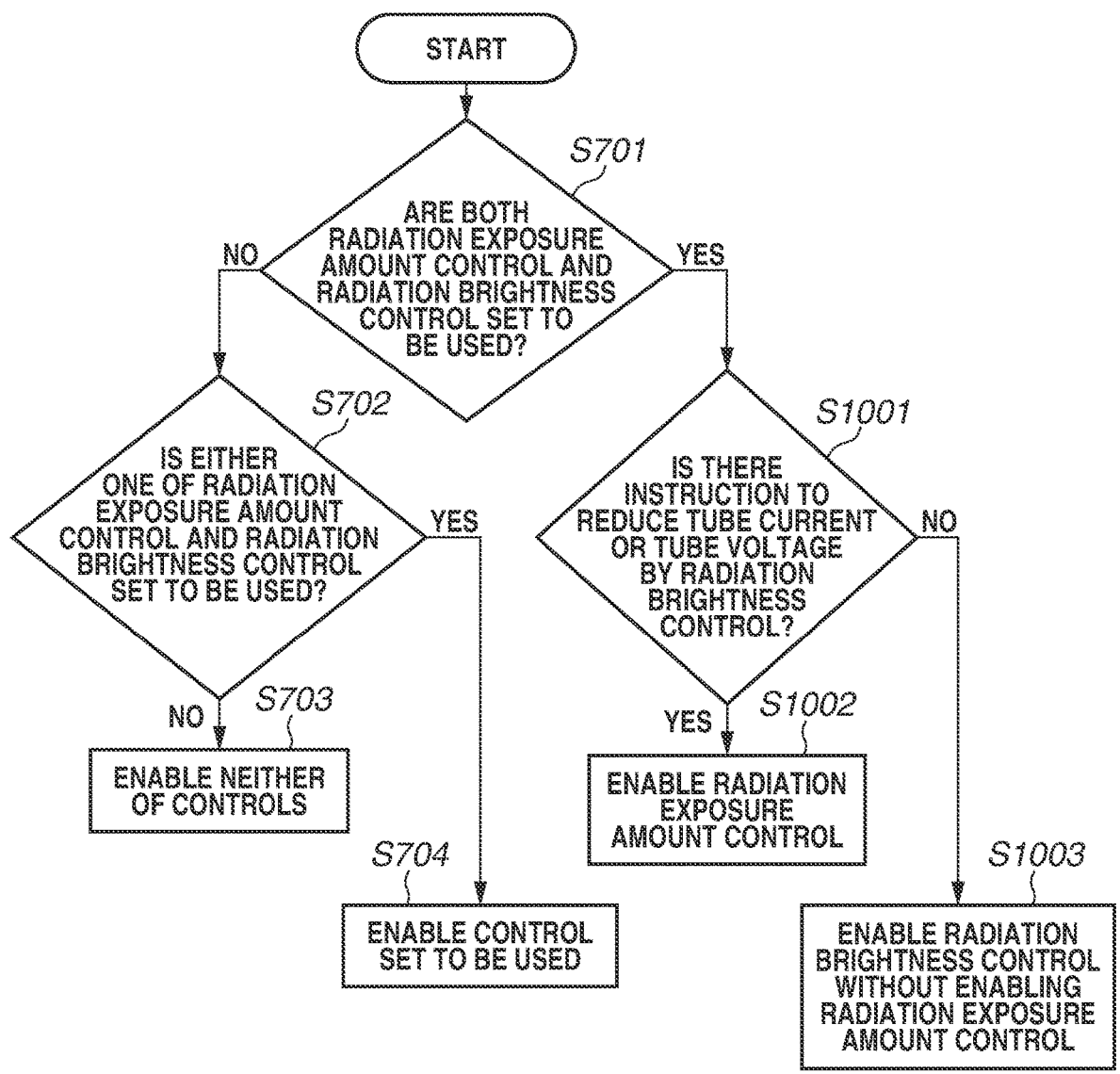
FIG. 10 is a flowchart illustrating a control method of the arbitration unit.

A sixth exemplary embodiment will be described below. FIG. 10 is a flowchart illustrating a control method of an arbitration unit 408 according to the sixth exemplary embodiment. FIG. 10 includes S1001 to S1003 instead of S705 to S707 of FIG. 7. Differences of the sixth exemplary embodiment from the third exemplary embodiment will be described below.

S701 to S704 are similar to those of FIG. 7. In S701, if the use of both the radiation exposure amount control and the radiation brightness control are set (YES in S701), the processing proceeds to S1001.

In S1001, the arbitration unit 408 determines whether the control apparatus 310 has instructed the radiation generation apparatus 324 to reduce the tube current or tube voltage (radiation condition) by the radiation brightness control. If there is an instruction to reduce the tube current or tube voltage (radiation condition) by the radiation brightness control (YES in S1001), the processing proceeds to S1002. If there is an instruction to increase the tube current or tube voltage (radiation condition) by the radiation brightness control (NO in S1001), the processing proceeds to S1003.

In S1002, the arbitration unit 408 enables the radiation exposure amount control and the radiation brightness control to use both the radiation exposure amount control and the radiation brightness control.

In S1003, the arbitration unit 408 enables the radiation brightness control without enabling the radiation exposure amount control. This can prevent the execution of conflicting operations, such as attempting to reduce the amount of radiations by the radiation exposure amount control and attempting to increase the amount of radiations by the radiation brightness control.

While exemplary embodiments have been described in detail above, some embodiments are not limited to such specific exemplary embodiments. Various changes and modifications can be made without departing from the gist of the present disclosure set forth in the claims.

Other Embodiments

Some embodiment(s) can also be realized by a computer of a system or apparatus that reads out and executes computer-executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer-executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer-executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the present disclosure, an appropriate radiation exposure amount can be controlled.

While the present disclosure has been described exemplary embodiments, it is to be understood that some embodiments are not limited to the disclosed exemplary embodiments. The scope of the following claims is to be accorded the broadest interpretation so as to encompass all such modifications and equivalent structures and functions.

This application claims priority to Japanese Patent Application No. 2018-245339, which was filed on Dec. 27, 2018, and to Japanese Patent Application No. 2019-177549, which was filed on Sep. 27, 2019, which are hereby incorporated by reference herein in their entireties.

What is claimed is:

1. A radiation imaging apparatus comprising:
an imaging area including a plurality of conversion elements configured to convert a radiation into an electrical signal;
a detection element provided in the imaging area and configured to detect the radiation;
a reading unit configured to read signals of the conversion elements and the detection element; and
a control unit configured to execute radiation exposure amount control in capturing a radiation image by a control method selected from between a first control method and a second control method based on an imaging condition in capturing the radiation image, the first control method controlling an exposure amount of the radiation based on the signal of the detection element read by the reading unit during radiation irradiation, the second control method controlling the exposure amount of the radiation based on a pixel value of the radiation image, the radiation image being based on the signals of the plurality of conversion elements read by the reading unit.

2. The radiation imaging apparatus according to claim 1, wherein the first control method includes controlling a stop of irradiation based on a cumulative exposure amount of the radiation,
wherein the imaging condition includes a frame rate and an irradiation time, and
wherein the control unit is configured to identify a time for enabling accumulation for the first control method based on the frame rate, and select the control method based on the time for enabling the accumulation and the irradiation time.

3. The radiation imaging apparatus according to claim 2, wherein the control unit is configured to, if the time for enabling the accumulation is greater than the irradiation time, select the first control method, and if the time enabling the accumulation is less than or equal to the irradiation time, select the second control method.

4. The radiation imaging apparatus according to claim 2, wherein the second control method includes setting an irradiation condition for radiation imaging after radiation imaging corresponding to the radiation image based on the pixel value of the radiation image, and
wherein the control unit is configured to, in performing the second control method, perform the first control method along with the second control method during a predetermined period from a start of the second control method.

5. The radiation imaging apparatus according to claim 4, wherein the control unit is configured to, in performing the second control method, perform the first control method along with the second control method during a period from the start of the second control method to when the irradiation condition is set by the second control method.

6. The radiation imaging apparatus according to claim 1, wherein a target region of the first control method and a target region of the second control method are the same.

7. The radiation imaging apparatus according to claim 1, wherein the control unit is configured to determine a threshold to be referred to by either one of the first and second control methods based on correlation data between control values of the respective first and second control methods and a threshold to be referred to by the other of the first and second control methods.

8. A radiation imaging apparatus comprising:
an imaging area including a plurality of conversion elements configured to convert a radiation into an electrical signal;
a detection element provided in the imaging area and configured to detect the radiation;
a reading unit configured to read signals of the conversion elements and the detection element; and
an arbitration unit configured to arbitrate between a first control method and a second control method, the first control method controlling an exposure amount of the radiation based on the signal of the detection element read by the reading unit during radiation irradiation, the second control method controlling the exposure amount of the radiation based on a pixel value of a radiation image, the radiation image being based on the signals of the plurality of conversion elements read by the reading unit.

9. The radiation imaging apparatus according to claim 8, wherein the arbitration unit is configured to, if use of the first and second control methods is set, enable either one of the first and second control methods.

10. The radiation imaging apparatus according to claim 8, wherein the arbitration unit is configured to, if use of the first and second control methods is set, enable either one of the first and second control methods based on an imaging method.

11. The radiation imaging apparatus according to claim 8, wherein the arbitration unit is configured to, if use of the first and second control methods is set, enable only the first control method for general radiography and enable only the second control method for fluoroscopic imaging.

12. The radiation imaging apparatus according to claim 8, wherein the arbitration unit is configured to, if use of the first and second control methods is set, use both the first and second control methods with higher priority given to either one of the first and second control methods based on an imaging method.

13. The radiation imaging apparatus according to claim 8, wherein the arbitration unit is configured to, if use of the first and second control methods is set, use both the first and second control methods in a case of general radiography, with higher priority given to the first control method, and use both the first and second control methods in a case of fluoroscopic imaging, with higher priority given to the second control method.

14. The radiation imaging apparatus according to claim 8, wherein the arbitration unit is configured to, if use of the first and second control methods is se, arbitrate between the first and second control methods so that an irradiation time of the radiation does not fall below a minimum irradiation time.

15. The radiation imaging apparatus according to claim 8, wherein the arbitration unit is configured to, if use of the first and second control methods is set, arbitrate between the first and second control methods so that a tube current or tube voltage does not fall below a minimum tube current or minimum tube voltage.

16. The radiation imaging apparatus according to claim 8, wherein the arbitration unit is configured to, if use of the first and second control methods is set and there is an instruction to reduce a tube current or tube voltage by the second control method, enable both the first and second control methods, and if there is an instruction to increase the tube current or tube voltage by the second control method, enable the second control method without enabling the first control method.

17. A radiation imaging system comprising:
a radiation source; and
the radiation imaging apparatus according to claim 1.

18. A control method to be executed by a radiation imaging apparatus including an imaging area including a plurality of conversion elements configured to convert a radiation into an electrical signal, a detection element provided in the imaging area and configured to detect the radiation, and a reading unit configured to read signals of the conversion elements and the detection element, the control method comprising:
performing radiation exposure amount control in capturing a radiation image by a control method selected from between a first control method and a second control method based on an imaging condition in capturing the radiation image, the first control method controlling an exposure amount of the radiation based on the signal of the detection element read by the reading unit during radiation irradiation, the second control method controlling the exposure amount of the radiation based on a pixel value of the radiation image, the radiation image being based on the signals of the plurality of conversion elements read by the reading unit.

19. A control method to be executed by a radiation imaging apparatus including an imaging area including a plurality of conversion elements configured to convert a radiation into an electrical signal, a detection element provided in the imaging area and configured to detect the radiation, and a reading unit configured to read signals of the conversion elements and the detection element, the control method comprising:

arbitrating between a first control method and a second control method, the first control method controlling an exposure amount of the radiation based on the signal of the detection element read by the reading unit during radiation irradiation, the second control method controlling the exposure amount of the radiation based on a pixel value of a radiation image, the radiation image being based on the signals of the plurality of conversion elements read by the reading unit.

20. A computer-readable storage medium storing a program for causing a computer to execute the control method according to claim 18.

\* \* \* \* \*